(12) United States Patent
Zhou

(10) Patent No.: US 8,437,837 B2
(45) Date of Patent: May 7, 2013

(54) METHOD AND APPARATUS FOR INDUCED T-WAVE ALTERNANS ASSESSMENT

(75) Inventor: Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1578 days.

(21) Appl. No.: 11/536,946

(22) Filed: Sep. 29, 2006

(65) Prior Publication Data

US 2008/0082133 A1   Apr. 3, 2008

(51) Int. Cl.
*A61B 5/04* (2006.01)
*A61N 1/00* (2006.01)

(52) U.S. Cl.
USPC .................................. 600/509; 600/5; 607/9

(58) Field of Classification Search ....... 607/9; 600/509
See application file for complete search history.

(56) References Cited

U.S. PATENT DOCUMENTS

| | | | |
|---|---|---|---|
| 5,117,824 A | 6/1992 | Keimel | |
| 5,265,617 A | 11/1993 | Verrier et al. | |
| 5,312,441 A | 5/1994 | Mader et al. | |
| 5,437,285 A * | 8/1995 | Verrier et al. | 600/515 |
| 6,393,316 B1 | 5/2002 | Gillberg et al. | |
| 6,453,191 B2 * | 9/2002 | Krishnamachari | 600/515 |
| 6,512,940 B1 | 1/2003 | Brabec et al. | |
| 6,522,915 B1 | 2/2003 | Ceballos et al. | |
| 6,622,046 B2 | 9/2003 | Fraley et al. | |
| 6,865,414 B1 * | 3/2005 | Levine | 600/510 |
| 6,957,105 B2 | 10/2005 | Pastore et al. | |
| 6,983,183 B2 * | 1/2006 | Thiagarajan et al. | 600/509 |
| 7,027,867 B2 * | 4/2006 | Park et al. | 607/25 |
| 2004/0002743 A1 | 1/2004 | Park et al. | |
| 2004/0186527 A1 | 9/2004 | Rouw et al. | |
| 2005/0049516 A1 | 3/2005 | Ideker | |
| 2005/0222513 A1 | 10/2005 | Hadley et al. | |
| 2005/0234355 A1 * | 10/2005 | Rowlandson | 600/509 |
| 2006/0116596 A1 | 6/2006 | Zhou et al. | |
| 2007/0255345 A1 * | 11/2007 | Krause | 607/59 |

FOREIGN PATENT DOCUMENTS

| | | |
|---|---|---|
| EP | 1050271 A | 8/2000 |
| WO | WO2004/062486 A | 7/2004 |
| WO | WO2006/060587 A | 8/2006 |

* cited by examiner

*Primary Examiner* — Nicole F Lavert
(74) *Attorney, Agent, or Firm* — Michael C. Soldner

(57) ABSTRACT

An implantable medical device and associated method assesses T-wave alternans. The method includes sensing a cardiac signal from implanted electrodes subsequent to a premature contraction; measuring a T-wave parameter from the sensed cardiac signal for a plurality of cardiac cycles; and determining a T-wave alternans metric corresponding to the measured T-wave parameter.

29 Claims, 8 Drawing Sheets

METHOD AND APPARATUS FOR INDUCED T-WAVE ALTERNANS ASSESSMENT

REFERENCE TO RELATED APPLICATIONS

This application is a continuation-in-part to U.S. Pat. Appl. Publication No. 2006/0116592, filed Jul. 21, 2005 and entitled "Method and apparatus for detection and monitoring of T-wave alternans", incorporated herein by reference in its entirety.

TECHNICAL FIELD

The invention relates generally to medical devices and, in particular, to a device and method for assessing T-wave alternans in a patient.

BACKGROUND

T-wave alternans is beat-to-beat alternation in the morphology, amplitude, and/or polarity of the T-wave, and can be observed on surface electrocardiogram (ECG) recordings. T-wave alternans (TWA) has been recognized in a variety of clinical conditions, including acquired and congenital long QT syndrome and ischemic heart disease associated with ventricular arrhythmias. TWA is considered an independent predictor for cardiac arrhythmias. Experimentally, TWA has been shown to be a precursor of ventricular tachycardia.

In past practice, TWA has been assessed from surface ECG recordings obtained in a clinical setting. The low-amplitude changes in the T-wave signal during TWA, which is on the order of microvolts, requires complicated software to assess TWA from a surface ECG recording of typically 128 heart beats or more during exercise or high-rate atrial pacing.

DETAILED DESCRIPTION

Figure 1:
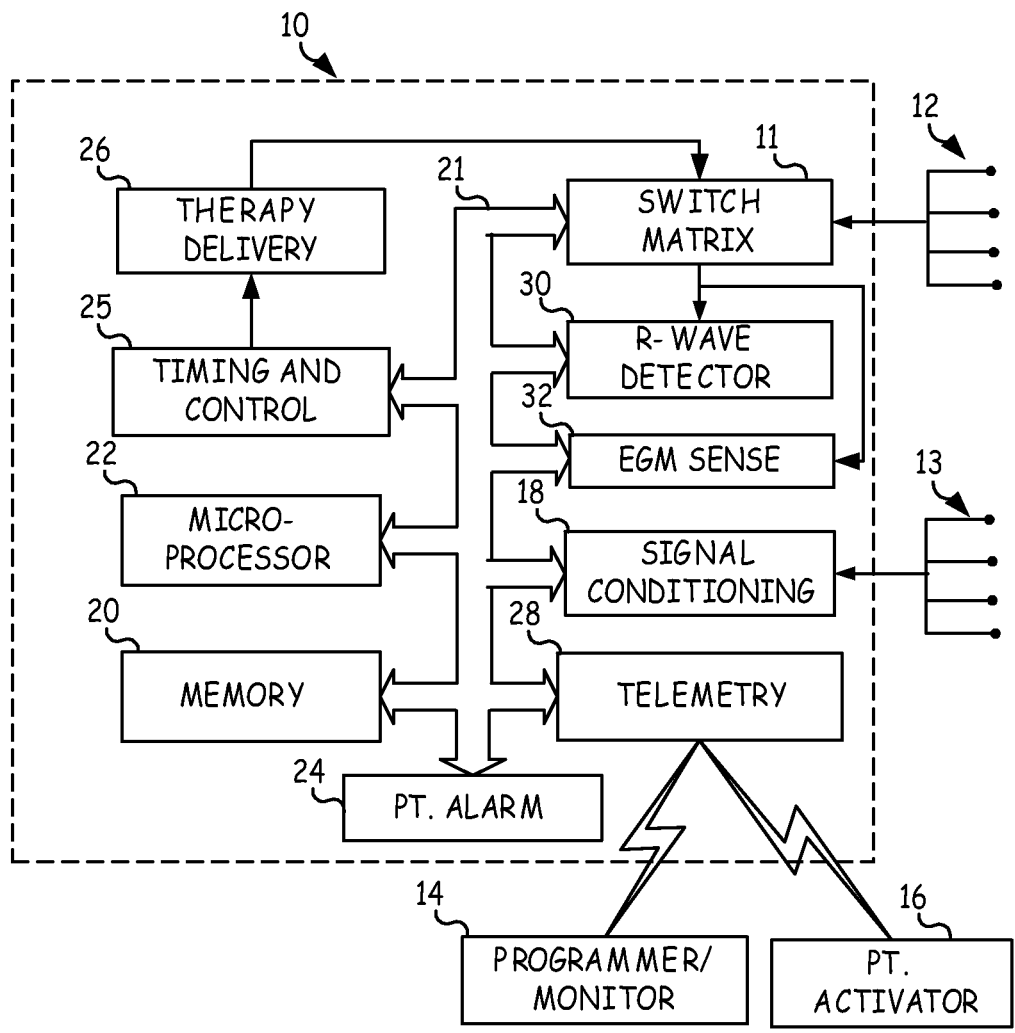
FIG. 1 is a functional block diagram of an IMD system that may be used for monitoring TWA.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a functional block diagram of an IMD system that may be used for monitoring TWA. The system provides for dynamic monitoring of TWA in an ambulatory patient. The system includes IMD 10 and associated electrodes 12 for acquiring EGM signals. EGM signals are used by IMD 10 for assessing cardiac rhythm for determining if and when a therapy is needed. IMD 10 further uses the acquired EGM signals for TWA assessment as will be described herein.

IMD 10 may also be coupled to one or more physiological sensors 13, such as an activity sensor or hemodynamic sensors, such as blood pressure sensors. Physiological signals may be used for detecting cardiac events such as arrhythmias or hemodynamic events. Physiological signals may be used by IMD 10 for triggering certain device operations. In one embodiment, physiological signals are used to trigger a TWA assessment.

IMD 10 is adapted for bidirectional communication with an external programmer/monitor 14 via telemetry circuitry 28. Programmer/monitor 14 is used for programming operating parameters in IMD 10 and for uplinking data from IMD 10. In accordance with one embodiment of the present invention, programmer/monitor 14 may be used by a clinician to initiate a TWA assessment. Alternatively, programmer/monitor 14 may be used to program parameters controlling an automated TWA assessment performed by IMD 10. A TWA report may be received by programmer/monitor 14 from IMD 10 including TWA data and/or TWA assessment results. In some embodiments, EGM data acquired by IMD 10 for use in TWA assessment may be transferred to programmer/monitor 14 for analysis by programmer/monitor 14 or another external computer system such as a remote patient management network. IMD 10 may also be adapted for communicating with a patient activator 16 which may be used by a patient or other caregiver to initiate a TWA assessment.

IMD 10 includes an R-wave detector 30, which receives EGM signals from electrodes 12 via switch matrix 11. R-wave detector 30 includes a sense amplifier having frequency response characteristics and beat-by-beat automatic adjusting sensitivity for accurate R-wave detection. R-wave detection may generally correspond to that disclosed in U.S. Pat. No. 5,117,824 issued to Keimel et al., U.S. Pat. No. 6,393,316 issued to Gilberg et al., or U.S. Pat. No. 5,312,441 issued to Mader, et al., all of which patents are incorporated herein by reference in their entirety.

IMD 10 further includes an EGM sense amplifier 32 that may be used for acquiring EGM signals for specialized signal analyses. EGM sense amplifier 32 receives signals from electrodes 12 via switch matrix 11. EGM sense amplifier 32 provides a wider band of frequency response than R-wave detector 30 and a separately adjustable gain setting. EGM sense amplifier 32 may be embodied as an automatic gain control sense amplifier enabled for automatic gain adjustment responsive to the amplitude of sensed T-wave signals. EGM signal segments for use in specialized analyses, such as TWA assessment, may be extracted from EGM signals obtained by sense amplifier 32 based on relative timing from R-waves detected by R-wave detector 30. In particular, T-wave signal analysis is performed to obtain T-wave measurements during a T-wave sensing window selected relative to an R-wave detection signal from R-wave detector 30.

Electrodes 12 may be located on leads extending from IMD 10 or may be leadless electrodes incorporated in or on the housing of IMD 10. R-wave detector 30 and EGM sense amplifier 32 receive signals from electrodes 12 via switch matrix 11. Switch matrix 11, under the control of microprocessor 22, is used for selecting which electrodes are coupled to R-wave detector 30 for reliable R-wave detection and which electrodes are coupled to EGM sense amplifier 32 for use in TWA assessment.

IMD 10 includes a signal conditioning module 18 for receiving EGM signals from EGM sense amplifier 32 and physiological signals from sensors 13. Signal conditioning module 18 includes sense amplifiers and may include other signal conditioning circuitry such as filters and an analog-to-digital converter. Microprocessor 22 receives signals from signal conditioning module 18 for detecting physiological events on system bus 21.

Memory 20 is provided for storing conditioned EGM signal output from conditioning module 18. In one embodiment, processing of EGM signals for assessing TWA is performed by IMD microprocessor 22. Microprocessor 22, controls IMD functions according to algorithms and operating parameters stored in memory 20. Microprocessor 22 may perform TWA assessment according to the methods to be described below. In response to TWA assessment results, microprocessor 22 may cause an alert signal to be generated by alarm circuitry 24. Additionally or alternatively, a therapy delivery module 26 may be signaled to deliver or withhold a therapy, or adjust therapy delivery parameters under the control of timing and control circuitry 25. In various embodiments, control circuitry implemented for performing automated TWA assessment in IMD 10 may include application specific integrated circuit (ASIC), an electronic circuit, a processor (shared, dedicated, or group) and memory that execute one or more software or firmware programs, a combinational logic circuit, or other suitable components that provide the described functionality. The implementation of TWA assessment provided herein is not limited to a particular type of system architecture.

In other embodiments, EGM data acquired by IMD 10 for use in TWA assessment may be stored in memory 20 and downlinked to external programmer/monitor 14. Processing circuitry included in programmer/monitor 14 may then perform a TWA assessment according to programmed-in algorithms. Reports of TWA assessment results may be generated by either IMD 10 or external programmer/monitor 14, for display, printing or electronic storage such that the results are available for review by a clinician.

Figure 2:
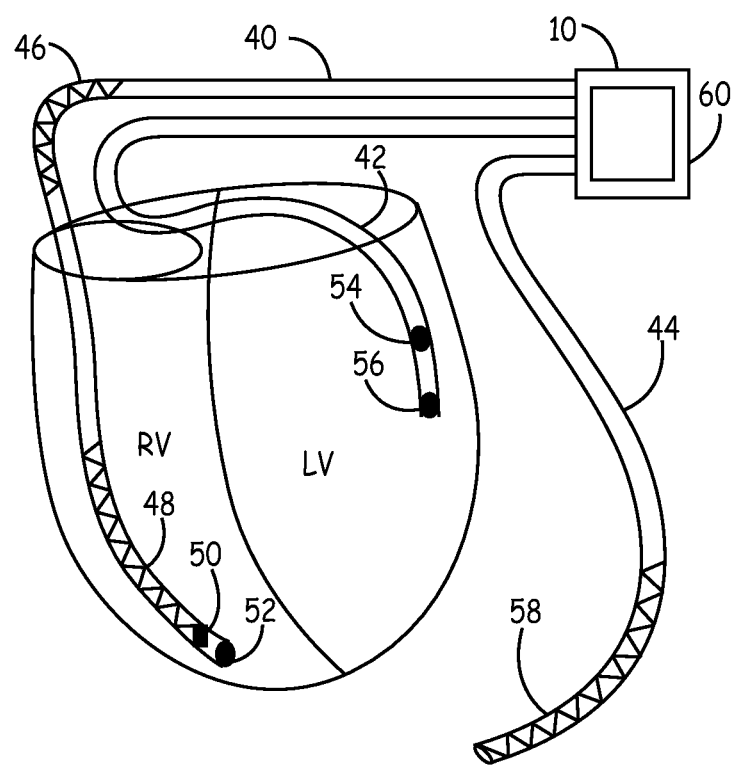
FIG. 2 illustrates one IMD configuration for acquiring EGM data in a TWA assessment method.

FIG. 2 illustrates one IMD configuration for acquiring EGM data in a TWA assessment method. IMD 10 may be embodied as any of a number of IMDs, such as a cardiac monitoring device, a pacemaker, an implantable cardioverter defibrillator, a neurostimulator, or a drug delivery device. EGM data suitable for assessing TWA may be acquired from signals sensed by subcutaneous electrodes, epicardial electrodes, transvenous or endocardial electrodes, or a neurostimulation lead. In one embodiment, multiple sensing vectors are selected for acquiring EGM data for TWA assessment. Multiple sensing vectors may be selected from any combination of available electrodes.

In the example shown in FIG. 2, IMD 10 is embodied as an implantable cardioverter defibrillator and is shown coupled to a set of leads adapted for delivering pacing, cardioversion, and defibrillation pulses and sensing EGM signals for detecting and discriminating heart rhythms. IMD 10 is coupled to a right ventricular (RV) lead 40 carrying a superior vena cava (SVC) coil electrode 46 and an RV coil electrode 48 for use in delivering cardioversion and defibrillation shock pulses. RV lead 40 carries a tip electrode 52 and a ring electrode 50 used in pacing and sensing functions in the right ventricle.

IMD 10 is further coupled to a coronary sinus (CS) lead 42 equipped with a tip electrode 56 and ring electrode 54 for use in sensing and pacing functions in the left heart chambers. CS lead 42 may be advanced into a cardiac vein so as to position CS tip electrode 56 and ring electrode 54 in a desired location over the left ventricle.

IMD 10 is provided with a can or case electrode 60 that may be used in combination with any of the cardiac electrodes for delivering stimulation pulses or sensing cardiac electrical signals in a unipolar mode. IMD 10 may be coupled to one or more subcutaneous leads 44 carrying a subcutaneous electrode 58, which may be a coil, patch or other type of electrode used in combination with SVC coil electrode 46, RV coil electrode 48, and/or can electrode 60 for delivering cardioversion or defibrillation shock pulses. Subcutaneous electrode 58 may alternatively be used in combination with any of the tip or ring electrodes 50, 52, 54 and 56 for sensing or pacing in unipolar modes.

Numerous sensing vectors may be selected from the electrodes available in the system shown in FIG. 2. Any electrode located on RV lead 40 or CS lead 42 may be selected in a unipolar sensing combination with can electrode 60 or subcutaneous electrode 58. Any combination of two electrodes located on RV lead 40 or CS lead 42 may be selected for bipolar sensing. Thus multi-vector sensing for TWA assessment may be achieved by selecting multiple unipolar and/or bipolar sensing electrode pairs, either simultaneously or sequentially, for collecting EGM signals. Both far-field and near-field EGM signals can be collected for TWA assessment. Multi-vector TWA analysis allows discrimination of concordant and discordant forms of TWA. The invention is not limited to the lead and electrode arrangement shown in Figure. 2. Numerous variations exist in the types of leads and electrodes that may be included in a system for monitoring TWA.

Figure 3:
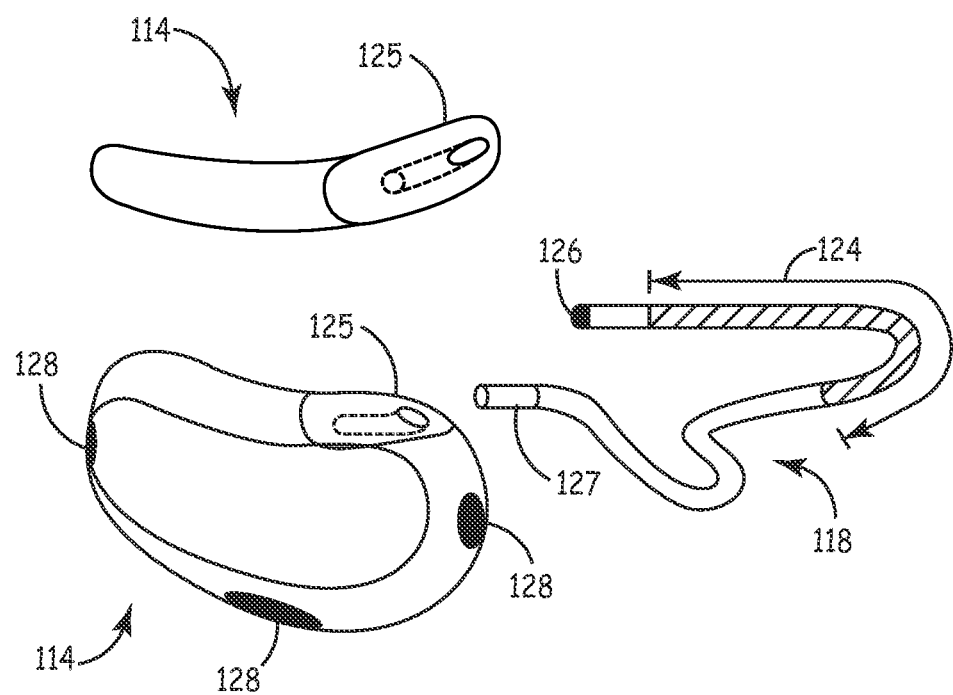
FIG. 3 is a frontal and plan view of a subcutaneous implantable cardiovertor defibrillator which may be used for acquiring ECG data in a TWA assessment method.

FIG. 3 is a frontal and plan view of a subcutaneous implantable cardioverter defibrillator (SubQ ICD) 114. The functionality represented by the block diagram of FIG. 1 may be implemented in a subcutaneous device such as SubQ ICD 114. TWA assessment methods described herein may rely on subcutaneous ECG sensing rather than intracardiac EGM sensing. SubQ ICD 114 is an ovoid and includes a substantially kidney-shaped profile forming a housing with a connector 125 for attaching a subcutaneous sensing and cardioversion/defibrillation therapy delivery lead 118.

Subcutaneous lead 118 includes of a distal defibrillation coil electrode 124, a distal sensing electrode 126, an insulated flexible lead body and a proximal connector pin 127 for connection to the housing of SubQ ICD 114 via connector 125. SubQ ICD 114 further includes a subcutaneous electrode array 128 welded into place on the flattened periphery of the housing of SubQ ICD 114. The SEA 128 is welded to SubQ ICD housing (to preserve hermaticity) and are connected via wires to electronic circuitry inside SubQ ICD 114. SEA 128 may be constructed of flat plates, or alternatively, spiral electrodes as generally described in U.S. Pat. No. 6,512,940 to Brabec, et al and mounted in a non-conductive surround shroud, as generally described in U.S. Pat. No. 6,522,915 to Ceballos, et al and U.S. Pat. No. 6,622,046 to Fraley, et al, all of which patents are incorporated herein by reference in their entireties. The SEA 128 shown in FIG. 2 includes three electrodes positioned to form orthogonal signal vectors. Any of the electrodes included in SEA 128 or on subcutaneous lead 118 may be selected in any combination for sensing subcutaneous ECG signals for use in TWA assessment. The methods described herein for assessing TWA hereinafter refer to the use of EGM signals, however, it is recognized that subcutaneous ECG signals may be substituted for EGM signals.

Figure 4:
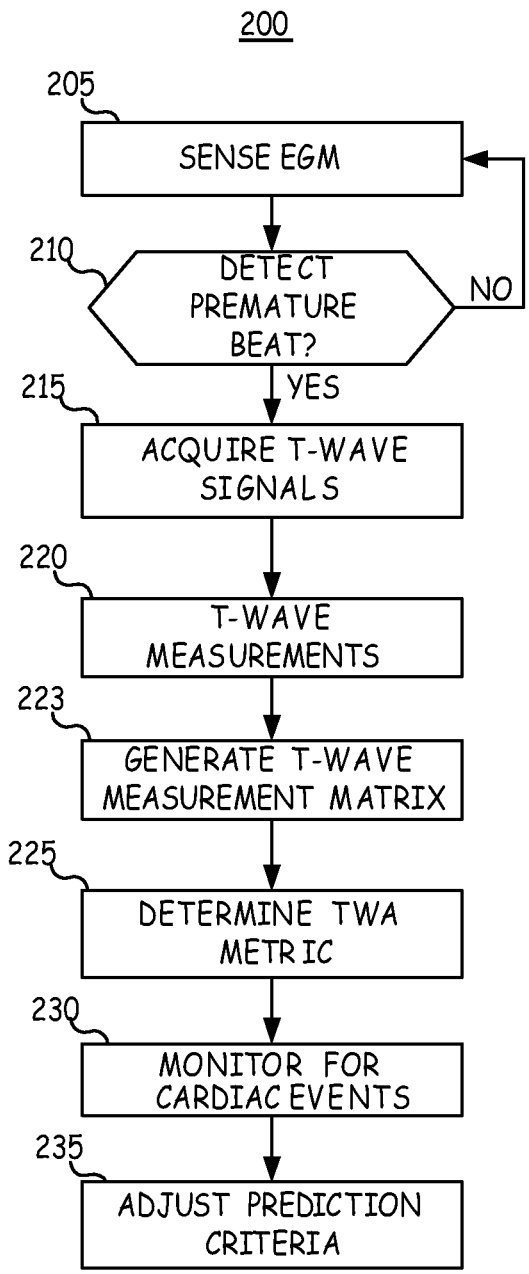
FIG. 4 is a flow chart summarizing a method for assessing TWA according to one embodiment of the invention.

FIG. 4 is a flow chart summarizing a method for assessing TWA according to one embodiment of the invention. Flow chart 200 is intended to illustrate the functional operation of an IMD system, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 200 for assessing TWA includes sensing an EGM signal at block 205 for monitoring for premature cardiac beats. At block 210, the EGM signal is analyzed to determine if a premature beat is detected. In one embodiment, premature beats are detected based on EGM signal interval analysis. For example, signals from an R-wave detector may be used for measuring R-R intervals, and a premature ventricular contraction (PVC) may be detected based upon R-R interval criteria. In addition or alternatively, premature beats may be detected based on EGM signal pattern analysis. For example, a premature ventricular contraction may be detected based on a pattern of two consecutive R-waves without an intervening P-wave sensed from the atria. In other embodiments, a detected premature beat may be an evoked premature beat in response to a premature pacing pulse, as will be described in greater detail herein.

If a premature beat is detected at decision block 210, T-wave signals are acquired by the IMD subsequent to the detected premature beat at block 215. Typically, a T-wave sensing window is set relative to detected R-waves for acquiring and storing a plurality of consecutive T-wave signals, for example 10 to 20 T-wave signals. T-wave signals may additionally be acquired prior to the premature beat. For example two to four T-wave signals preceding the premature beat may be stored. The current heart rate (HR) and/or the premature beat interval, e.g. the interval between a detected R-wave and a subsequent premature ventricular contraction, may be recorded at block 215 for use in determining a TWA metric. Generally, if a TWA episode occurs, it will occur during an elevated heart rate. Depending on a disease state or other physiological conditions, a longer TWA episode or an episode having greater differences between alternating T-waves may occur at relatively lower heart rates. The interval at which a premature beat occurs may also affect whether a TWA episode occurs and may reflect the severity of a pathological condition. As such, the HR and/or premature beat interval corresponding to a TWA episode precipitating from a premature beat may be used in determining a TWA metric.

Figure 5:
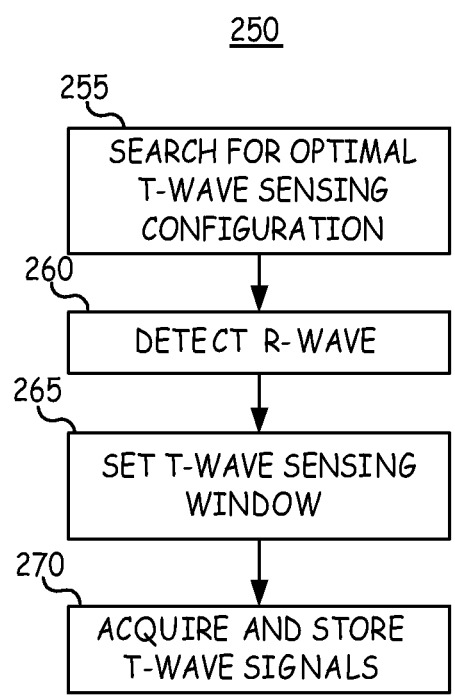
FIG. 5 is a flow chart summarizing one method for acquiring T-wave signals for use in a TWA assessment.

One method for acquiring T-wave signals at block 215 is summarized by the flow chart shown in FIG. 5. At block 255 of flow chart 250, an optimal T-wave sensing configuration is identified. Searching for an optimal T-wave sensing configuration may include selecting multiple sensing vectors using the available electrodes and adjusting sensing parameters such as the gain of sense amplifiers. Identifying an optimal T-wave sensing configuration generally involves identifying the sensing configuration providing the highest T-wave amplitude and/or greatest signal-to-noise ratio during the T-wave sensing window. R-waves are detected at block 260 for multiple consecutive cardiac signals subsequent to the detected premature beat. R-wave detection may be performed using a nominal electrode sensing configuration with a different gain setting than the optimal T-wave sensing configuration and gain setting identified for acquiring T-wave signals.

At block 265, a T-wave sensing window is set relative to the detected R-wave for each of a selected number of consecutive cardiac cycles subsequent to the detected premature beat. T-wave signals are acquired and stored for each cardiac cycle using the optimal sensing configuration and gain setting at step 270. It is recognized that T-wave signals may be acquired using multiple sensing configurations, either simultaneously or sequentially. Methods for acquiring T-wave signals for TWA assessment are generally described in U.S. Pat. Pub. No. 2006/0116592, incorporated herein by reference in its entirety.

Referring again to FIG. 4, at block 220, T-wave measurements are performed using the acquired T-wave signals. T-wave measurements may include any feature of the T-wave signal known to alternate during a TWA episode. Among the T-wave measurements that may be made are T-wave amplitude and T-wave area (integral). The T-wave measurements made for multiple consecutive cardiac cycles are used to generate a T-wave measurement matrix at block 223. Data matrix formation includes assigning every other T-wave measurement an "A" label and intervening T-wave measurements a "B" label. T-wave measurements are then stored in a matrix according to "A" and "B" labels. In one embodiment, T-wave amplitudes are measured and a matrix of "A" T-wave amplitudes and "B" T-wave amplitudes is generated. T-wave amplitudes may be measured as an average signal voltage, a peak voltage relative to a baseline amplitude such as the amplitude measured just prior to a sensed R-wave, or a peak-to-peak voltage difference. The net change in T-wave amplitudes can be calculated based on the difference between A and B T-waves measured immediately after a premature beat and the difference between alternating T-waves measured just prior to the premature beat.

In other embodiments, other T-wave parameters may be measured for generating the data matrix at block 223. Morphological features could be determined such as a T-wave template, T-wave width at a given threshold crossing, or other features that allow TWA to be distinguished by measuring consistent differences between "A" and "B" T-wave measurements. When larger number of T-wave signals are sampled, spectral analysis may alternatively be performed in which frequency-domain measurements are used in generating the data matrix for "A" and "B" labeled T-wave measurements. Any T-wave parameter that allows the A-B-A-B-A-B pattern of TWA to be ascertained may be measured at block 220.

At block 225, one or more TWA metrics are determined by comparative analysis of the "A" and "B" labeled T-wave measurements stored in the data matrix generated at block 223. T-wave measurements may be compared on a beat-to-beat basis to determine the difference between "A" labeled T-wave measurements and "B" labeled T-wave measurements. In the example given above in which T-wave amplitude measurements are stored, the beat-to-beat amplitude difference between "A" labeled T-wave measurements and "B" labeled T-wave measurements is calculated. The TWA metric obtained at block 225 could then be computed as the average of the differences between the "A" and "B" T-wave measurement pairs.

Alternatively or additionally, T-wave measurements may be averaged for all of the respective "A" and "B" labeled measurements. The difference between the averaged "A" measurement and the averaged "B" measurement may then be determined. In the example of T-wave amplitude measurements, all "A" amplitudes may be averaged to determine a mean "A" T-wave amplitude. All "B" amplitudes may be averaged to determine a mean "B" T-wave amplitude. The TWA metric determined at block 225 would then be computed as the difference between the average "A" T-wave amplitude and the average "B" T-wave amplitude.

The operations performed at block 225 may therefore include determining differences in "A" and "B" T-wave measurements on a beat-by-beat basis and further performing statistical analysis on the differences to determine an overall TWA metric. Alternatively, statistical analyses may be performed on the "A" and "B" T-wave measurements stored in the data matrix to determine mean or median "A" and "B" T-wave measurements. The difference between the means or medians may then be used to compute an overall TWA metric.

At block 225, determination of a TWA metric can alternatively be performed using daily averaging method that averages all T-wave measurements performed following all premature beats over a twenty-four hour, or other predetermined, time interval. The daily averaging method can reduce noise effects and be used to monitor the progression of cardiac disease involving the impairment of calcium cycling by comparing a daily average to a previous average.

As described in the previously-incorporated '592 published application, the T-wave measurements may be evaluated for possible contamination due to artifacts or signal noise. This evaluation is based on the differences between "A" and "B" T-wave measurements occurring in the T-wave signals. If TWA is present, the differences in the "A" and "B" T-wave measurements will be consistent in phase evidencing an A-B-A-B-A-B pattern. For example, if T-wave amplitudes are measured, the "A" T-wave amplitudes will be greater than the "B" T-wave amplitudes most of the time or less than the "B" T-wave amplitudes most of the time. Considerable variation in the comparative relation of the "A" and "B" T-wave measurements does not evidence an alternans pattern. As such, determination of a TWA metric may include verification that the beat-to-beat differences between "A" and "B" T-wave measurements are consistent in phase.

If the differences are changing in phase, i.e., "A" measurements are sometimes greater and sometimes less than "B" measurements, the TWA measurement may not be clinically meaningful. The TWA consistency may be evaluated by determining the percentage of all beat-to-beat differences being of the same phase.

Other TWA metrics may relate to the duration of the TWA episode or the decay of the alternating T-wave pattern, the heart rate during which the TWA episode occurred and the interval of the premature beat.

The IMD may operate in two modes for assessing TWA. In a first "learning" mode, the IMD may determine TWA metrics and "learn" criteria based on the TWA metric for predicting a cardiac event. Cardiac events that may be predicted based on a TWA assessment include arrhythmias, including tachycardia and fibrillation, and hemodynamic events. The IMD may "learn" prediction criteria based on the occurrence of such events and the correspondence to the most recently determined TWA metric as well as previously determined TWA metrics. As such, the IMD monitors for cardiac events at block 230 and adjusts a cardiac event prediction criteria at block 235 based on the currently determined TWA metric and whether or not a cardiac event was detected subsequent to the TWA episode at block 230. In this way, the IMD "learns" the severity of a TWA episode which precipitates a cardiac event.

Figure 6:
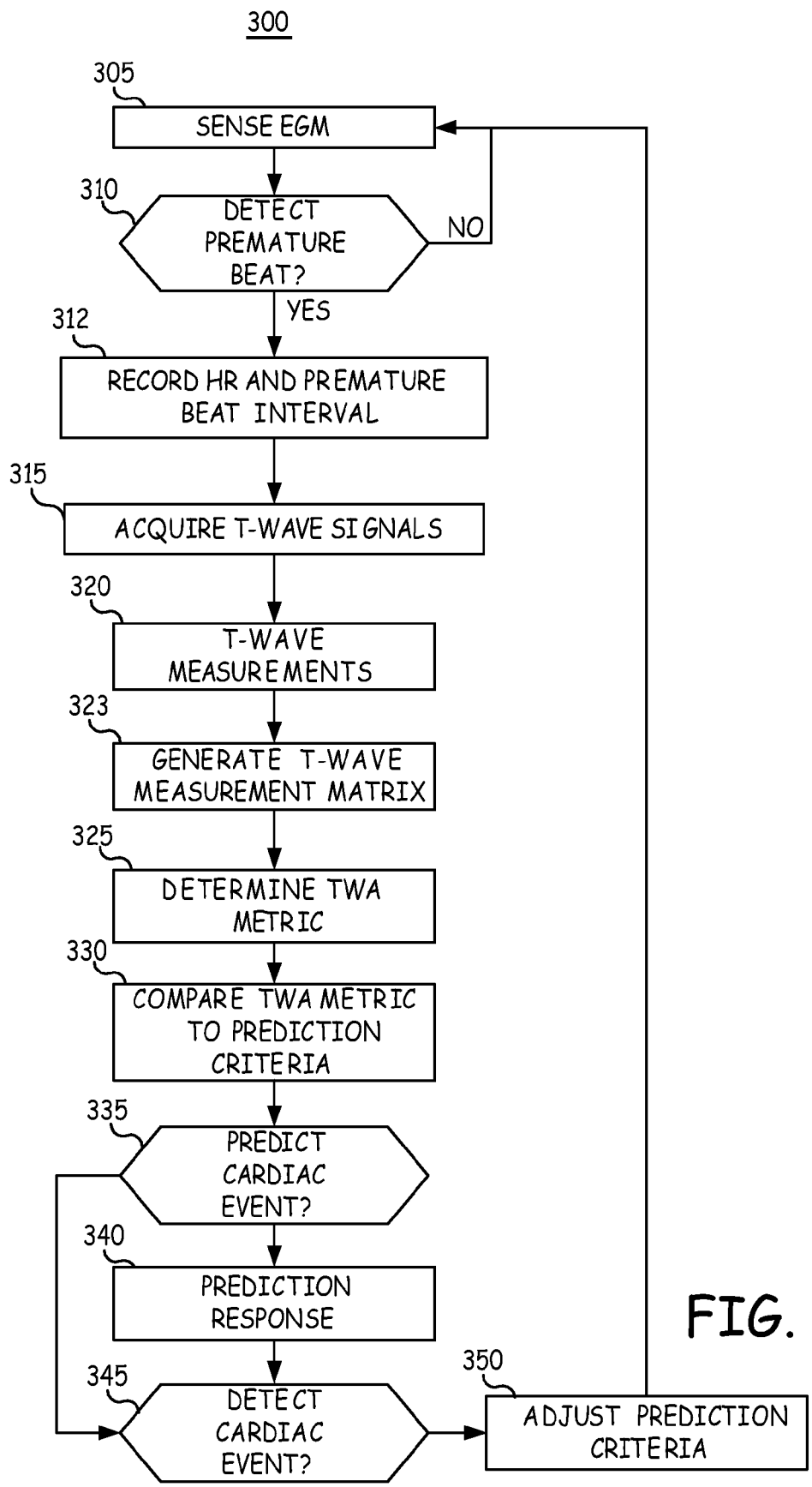
FIG. 6 is a flow chart summarizing a second operating mode of an IMD for monitoring TWA.

FIG. 6 is a flow chart summarizing a second operating mode of an IMD for monitoring TWA. In the second operating mode, the IMD automatically determines TWA metrics for predicting the occurrence of cardiac events. Method 300 includes sensing the EGM signal at block 305, and detecting a premature beat at block 310, which may be either an intrinsic or an evoked premature beat induced by delivering a premature pacing pulse. At block 312 the heart rate (HR) may be recorded and the interval of the premature beat may be recorded for use in determining a TWA metric. At block 315, T-wave signals are acquired subsequent to the detected premature beat, and one or more T-wave features are measured at block 320. Method 300 further includes generating a T-wave measurement matrix at block 323 and determining a TWA metric from the T-wave measurements at block 325. Alternatively, a T-wave metric is determined from the heart rate and or premature beat interval after verifying a TWA episode has occurred based on T-wave measurements.

At block 330 the TWA metric is compared to predetermined prediction criteria. If a cardiac event is predicted based on this comparison, as determined at decision block 335, a prediction response is provided at block 340. A cardiac event may be an arrhythmia, particularly life-threatening arrhythmias, a hemodynamic event such as an acute decompensation of congestive heart failure, or a slowly worsening of cardiac disease progression including impairment of intracellular calcium cycling. A response to a predicted cardiac event may include adjusting a therapy or delivering a preventative therapy (e.g., an electrical stimulation therapy or drug therapy) and/or triggering a patient and/or clinician alarm.

The prediction criteria may be adjusted at block 350 according to whether a cardiac event was detected at decision block 345, subsequent to a TWA episode. If a cardiac event is predicted but does not occur, the prediction criteria may be adjusted to be less sensitive, taking into account the most-recently determined TWA metric. If a cardiac event is detected but was not predicted, the prediction criteria may be adjusted to be more sensitive, taking into account the most-recently determined TWA metric. After making any appropriate adjustments to the predication criteria based on the presently-determined TWA metric and the presence or absence of a cardiac event, method 300 continues to monitor the EGM for a premature beat by returning to block 305.

Figure 7:
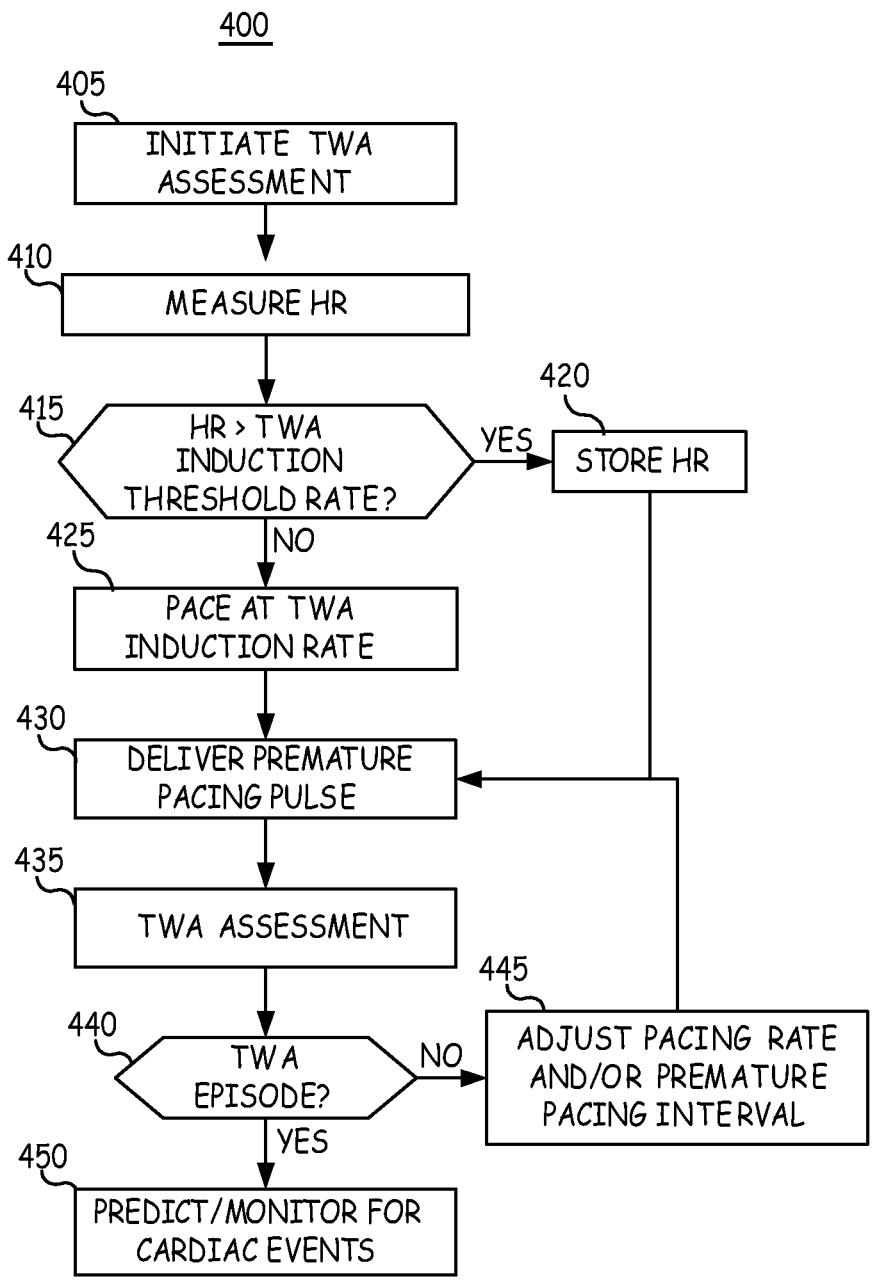
FIG. 7 is a flow chart summarizing a method for delivering a premature beat for inducing TWA.

FIG. 7 is a flow chart summarizing method 400 for delivering a premature beat for inducing TWA. TWA assessment may occur in response to detecting an intrinsic premature beat. For example, the IMD may trigger a TWA assessment in response to every premature ventricular contraction detected. In the case of frequent premature ventricular contractions, a minimum time between TWA assessments may be required. However, intrinsic premature beats may not occur as regularly or frequently as TWA assessment is desired. Accordingly, TWA may be induced by providing a pacing-induced premature beat.

At block 405 of method 400, a TWA assessment is initiated. TWA assessment may be performed on a periodic, scheduled or triggered basis or in response to a user command. At block 410, the heart rate is measured. The heart rate is compared to a predetermined minimum rate for inducing TWA at block 415. If the heart rate is greater than the TWA induction threshold, the heart rate is stored at block 420 and a premature pacing pulse is delivered at a predetermined premature interval at block 430. For example, a ventricular pacing pulse is delivered at a short pacing interval following a sensed R-wave.

If the heart rate is not greater than a TWA induction threshold rate, as determined at decision block 415, the IMD may pace the heart at a predetermined TWA induction pacing rate at block 425. The TWA induction pacing rate may be a rate greater than approximately 80 beats per minute, for example the TWA induction pacing rate may approximately 90 to 110 beats per minute. Pacing at the TWA induction pacing rate is performed for a predetermined interval of time, for example 10 to 30 cardiac cycles, though longer and shorter intervals may be used. At block 430, a premature pacing pulse is delivered at a predetermined premature pacing interval following the last of the pacing pulses delivered at the TWA induction pacing rate. The premature pacing pulse may be delivered at approximately 300 to 500 ms following the last pacing pulse, however other premature pacing pulses may be used and will depend on the heart rate at the time of delivering the premature pacing pulse for inducing TWA.

Following the premature pacing pulse, pacing at the TWA induction pacing rate may continue, pacing at another rate may continue or no pacing may be delivered. TWA assessment is performed at block 435, as described previously. Briefly, a desired number of T-wave signals are acquired just before and subsequent to the premature pacing pulse and T-wave measurements are performed for use in computing a TWA metric. At block 440, an induced TWA episode is verified based on the TWA assessment performed at block 435. If a TWA episode did not occur or the TWA metric was below a predetermined TWA verification threshold, the pacing rate may be increased and/or the premature pacing interval may be shorted at block 445. A repeated attempt at inducing TWA may be made by returning to block 430 for delivering a premature pacing pulse during the higher pacing rate and/or at the shortened premature pacing interval. Delivery of a premature pacing pulse may be repeated at multiple pacing rates or intrinsic heart rates and/or at multiple premature pacing intervals until a TWA episode is verified.

If a TWA episode is verified at block 440, the IMD may predict an increased risk for a cardiac event based on the TWA metric and/or monitor for the occurrence of cardiac events for use in adjusting cardiac event prediction criteria at block 450.

Figure 8:
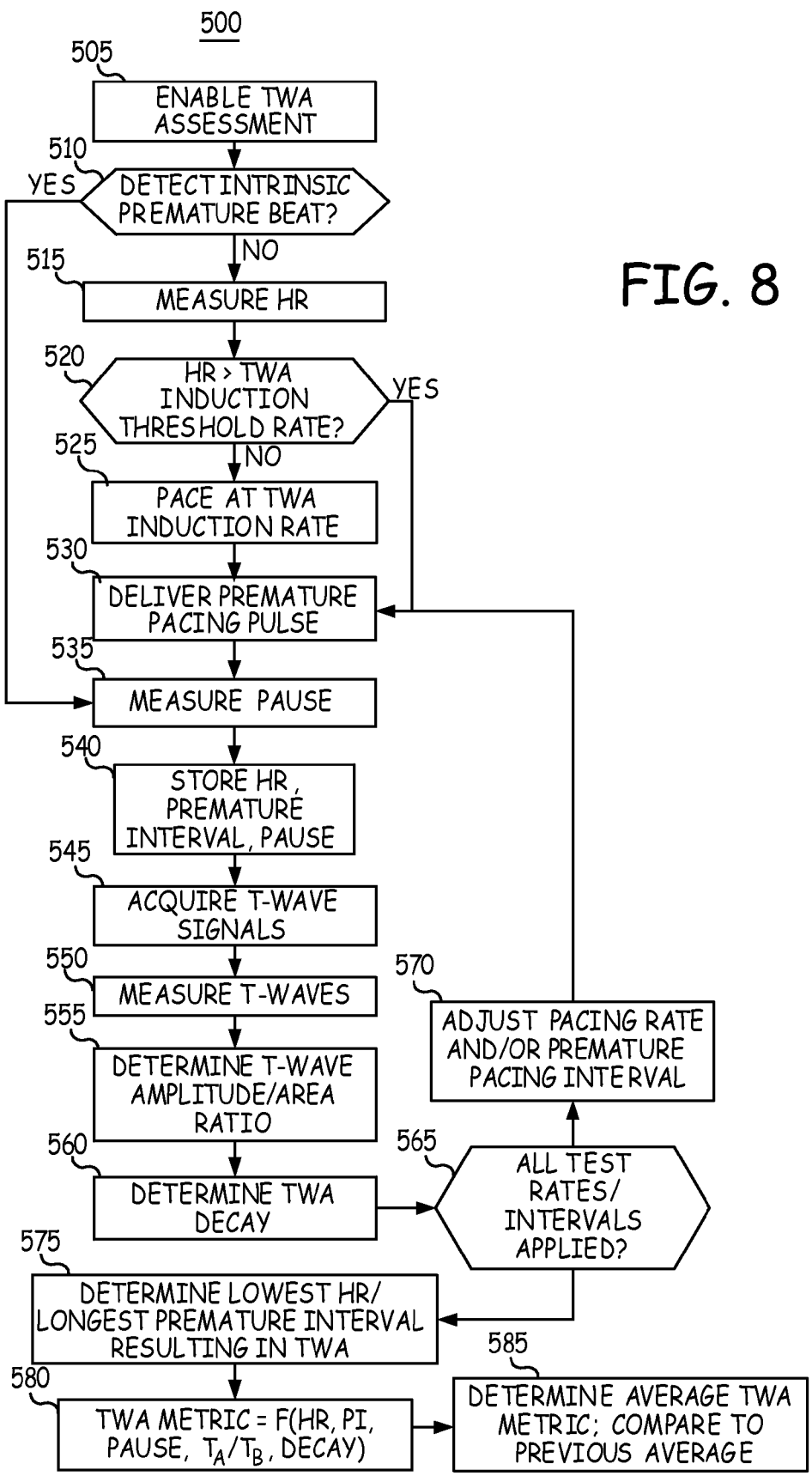
FIG. 8 is a flow chart of one method for determining a TWA metric and monitoring cardiac disease progression.

FIG. 8 is a flow chart of one method 500 for determining a TWA metric and monitoring cardiac disease progression. At block 505, TWA assessment is enabled. A TWA metric may be determined following detection of an intrinsic premature beat or following a pacing-induced premature beat. If no intrinsic premature beat is detected at decision block 510, the heart rate is measured at block 515. If the intrinsic HR is greater than a TWA induction threshold rate as determined at decision block 520, a pacing pulse is delivered at a predetermined premature interval at block 530. If the intrinsic HR is less than the TWA induction threshold rate, the heart is paced at a TWA induction pacing rate at block 525. A premature pacing pulse is then delivered at block 530 to induce TWA.

At block 535, the compensatory pause that normally follows a premature beat may be measured. The length of the premature interval will generally affect the length of the compensatory pause, which in turn can affect whether a TWA episode will occur and the characteristics (or severity) of the TWA episode.

At block 540, the heart rate, the premature interval, and the length of the compensatory pause are stored. At block 545, T-wave signals are acquired subsequent to the premature beat. The T-waves are measured at block 550 and T-wave measurements are stored in a matrix to allow comparison of "A" and "B" T-wave measurements. At block 555, the T-wave measurements are used to determine a ratio or difference of the T-wave "A" and "B" amplitudes, areas, widths, or other signal features.

At block 560, the TWA decay is measured. The TWA decay may be may be determined according to a number of methods. For example, TWA decay may be measured in time by determining the amount of time required following the premature beat for the ratio of the "A" T-wave measurement to the "B" T-wave measurement to be approximately 1 or within a given range greater than or less than 1. Alternatively, the TWA decay may be measured as a slope of a linear fit of the "A" or "B" T-wave measurements returning to a baseline T-wave over time.

Method 500 may involve measuring TWA at multiple TWA induction pacing rates to determine the lowest pacing rate at which TWA occurs in response to a premature beat. Method 500 may additionally or alternatively involve measuring TWA at multiple premature beat intervals to determine the longest premature beat interval which results in a TWA episode. Accordingly, if all test pacing rates and/or premature pacing intervals have not yet been applied, as determined at block 565, the TWA induction pacing rate and/or premature pacing interval may be adjusted at block 570. Method 500 returns to block 530 to repeat the TWA measurements.

After all test pacing rates and premature pulse intervals have been applied, a TWA metric is determined. At block 575, the lowest HR and/or longest premature interval at which a TWA episode occurred may be determined and stored. In a healthy heart, the myocytes can handle calcium cycling in a short time so that TWA episodes generally occur only at relatively high heart rates or in response to relatively short premature beat intervals, if at all. In a more diseased state, the TWA may occur at relatively lower heart rates and in response to longer premature beat intervals because the myocyte calcium handling ability is compromised. As such, either of or both the heart rate and premature beat interval resulting in TWA may be used in determining a TWA metric.

At block 580 a TWA metric is determined. The TWA metric may be determined as a function of one or more of a heart rate corresponding to a TWA episode, a premature beat interval corresponding to a TWA episode, a compensatory pause corresponding to a TWA episode, a ratio of or difference between the "A" and "B" T-wave measurements, and a TWA decay.

At block 585, a long term average of the TWA metric is determined from the currently determined TWA metric and one or more previously determined TWA metric. In one embodiment, a daily TWA metric average is computed at block 585 using multiple TWA metrics each computed subsequent to an intrinsic or paced premature beat. A daily or other long-term average of TWA metrics may be compared to previously determined averages for assessing the progression of a cardiac disease state. In particular, a trend of the average TWA metric may reflect changes in the calcium cycling properties of the myocardium, evidencing a worsening or improving cardiac disease state.

Thus, a system and method for assessing TWA have been presented in the foregoing description with reference to specific embodiments. It is appreciated that various modifications to the referenced embodiments may be made without departing from the scope of the invention as set forth in the following claims.

The invention claimed is:
1. A method, comprising:
    identifying a premature contraction in the heart of a patient;

sensing a cardiac signal from an implanted electrode subsequent to the premature contraction;
measuring a T-wave parameter from the sensed cardiac signal for a plurality of cardiac cycles in response to identifying the premature contraction; and
determining a T-wave alternans metric corresponding to the measured T-wave parameter.

2. The method of claim 1 wherein identifying the premature contraction comprises detecting a spontaneous premature contraction.

3. The method of claim 1 wherein identifying the premature contraction comprises delivering a cardiac pacing pulse at a predetermined interval corresponding to an evoked premature contraction.

4. The method of claim 3 wherein delivering the cardiac pacing pulse at the predetermined interval further comprises measuring a heart rate and comparing the heart rate to a predetermined T-wave alternans induction rate.

5. The method of claim 3 wherein delivering the cardiac pacing pulse at the predetermined interval further comprises pacing the heart at a T-wave alternans induction pacing rate.

6. The method of claim 1 wherein measuring the T-wave parameter comprises setting a T-wave measurement window.

7. The method of claim 1 wherein measuring the T-wave parameter comprises measuring one of a T-wave signal amplitude, a T-wave signal area, and a T-wave signal width.

8. The method of claim 1 wherein measuring the T-wave parameter comprises measuring a first T-wave parameter corresponding to a first T-wave morphology and measuring a second T-wave parameter corresponding to a second T-wave morphology.

9. The method of claim 8 wherein the T-wave alternans metric corresponds to a rate of decay of the difference between the first T-wave parameter and the second T-wave parameter.

10. The method of claim 8 further comprising:
verifying a T-wave alternans episode corresponding to the first T-wave parameter and the second T-wave parameter, wherein deteimining the T-wave alternans metric comprises determining a heart rate corresponding to the verified T-wave alternans episode.

11. The method of claim 8 further comprising:
verifying a T-wave alternans episode corresponding to the first T-wave parameter and the second T-wave parameter; and
wherein determining the T-wave alternans metric comprises determining a premature beat interval corresponding to the verified T-wave alternans episode.

12. The method of claim 8 further comprising:
verifying a T-wave alternans episode corresponding to the first T-wave parameter and the second T-wave parameter; and
wherein determining the T-wave alternans metric comprises determining a compensatory pause corresponding to the verified T-wave alternans episode.

13. The method of claim 1 further comprising:
comparing the T-wave alternans metric to a cardiac event prediction criteria; and
predicting a cardiac event based on the comparison.

14. The method of claim 1 further comprising:
determining an average of a plurality of T-wave alternans metrics each being computed subsequent to a plurality of premature beats; and
comparing the average to a previously determined average.

15. A computer-readable medium for storing a set of instructions which when implemented in an implantable medical device system cause the system to:
identify a premature contraction in the heart of a patient;
sense a cardiac signal from implanted electrodes subsequent to the premature contraction;
measure a T-wave parameter from the sensed cardiac signal for a plurality of cardiac cycles; and
determine a T-wave alternans metric corresponding to the measured T-wave parameter.

16. A system, comprising:
an implanted electrode for sensing cardiac signals; and
a processor for receiving the cardiac signals, the processor identifying a premature contraction in the heart of a patient and measuring a T-wave parameter from the sensed cardiac signals in response to identifying the premature contraction, the processor measuring the T-wave parameter for a plurality of cardiac cycles subsequent to the premature contraction and determining a T-wave alternans metric corresponding to the measured T-wave parameter.

17. The system of claim 16 wherein the premature contraction is a spontaneous premature contraction and wherein the processor is configured to detect the spontaneous premature contraction.

18. The system of claim 16 wherein the premature contraction is an evoked premature contraction and further comprising a therapy delivery module coupled to the processor for delivering a cardiac pacing pulse at a predetermined interval corresponding to the evoked premature contraction.

19. The system of claim 18 wherein the processor is configured to determine a heart rate and compare the heart rate to a predetermined T-wave alternans induction rate, and wherein the therapy delivery module delivers the cardiac pacing pulse at the predetermined interval in response to the heart rate being at least the T-wave alternans induction rate.

20. The system of claim 19 wherein the therapy delivery module paces the heart at a T-wave alternans induction pacing rate prior to delivering the cardiac pacing pulse at the predetermined interval corresponding to the evoked premature contraction.

21. The system of claim 16 wherein measuring the T-wave parameter comprises measuring a first T-wave parameter corresponding to a first T-wave morphology and measuring a second T-wave parameter corresponding to a second T-wave morphology.

22. The system of claim 16 wherein the T-wave alternans metric corresponds to a rate of decay of the difference between a first T-wave parameter and a second T-wave parameter.

23. The system of claim 16 wherein the processor is configured to verify a T-wave altemans episode corresponding to a first T-wave parameter and a second T-wave parameter, and wherein determining the T-wave alternans metric comprises determining a heart rate corresponding to the verified T-wave alternans episode.

24. The system of claim 16 wherein the processor is configured to verify a T-wave alternans episode corresponding to a first T-wave parameter and a second T-wave parameter, and wherein determining the T-wave alternans metric comprises determining a premature beat interval corresponding to the verified T-wave alternans episode.

25. The system of claim 24 wherein the premature beat interval corresponds to a maximum premature beat interval.

26. The system of claim 16 wherein the processor is configured to verify a T-wave alternans episode corresponding to a first T-wave parameter and a second T-wave parameter, and wherein determining the T-wave alternans metric comprises determining a compensatory pause corresponding to the verified T-wave alternans episode.

27. The system of claim 16 wherein the processor is configured to compare the T-wave alternans metric to a cardiac event prediction criterion and predict a cardiac event based on the comparison.

28. The system of claim 27 further comprising one of an alert module and a therapy delivery module responsive to the prediction of a cardiac event.

29. The system of claim 16 wherein the processor is configured to determine an average of a plurality of T-wave alternans metrics each computed subsequent to identified contractions and compare the average to a previously determined average.

* * * * *

UNITED STATES PATENT AND TRADEMARK OFFICE
CERTIFICATE OF CORRECTION

PATENT NO. : 8,437,837 B2  
APPLICATION NO. : 11/536946  
DATED : May 7, 2013  
INVENTOR(S) : Xiaohong Zhou Page 1 of 1

It is certified that error appears in the above-identified patent and that said Letters Patent is hereby corrected as shown below:

In the Claims:

Col. 12, line 49, claim 23, line 2, delete "altemans" and insert in place thereof -- alternans --.

Signed and Sealed this  
Third Day of September, 2013

Teresa Stanek Rea  
*Acting Director of the United States Patent and Trademark Office*